United States Patent
Wakao et al.

(10) Patent No.: US 8,763,587 B2
(45) Date of Patent: Jul. 1, 2014

(54) ABNORMALITY DETECTION DEVICE FOR INTERNAL COMBUSTION ENGINE

(75) Inventors: Kazuhiro Wakao, Susono (JP); Mie Sasai, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 13/519,633

(22) PCT Filed: Dec. 28, 2010

(86) PCT No.: PCT/JP2010/073760
§ 371 (c)(1),
(2), (4) Date: Jun. 28, 2012

(87) PCT Pub. No.: WO2012/090315
PCT Pub. Date: Jul. 5, 2012

(65) Prior Publication Data
US 2013/0263824 A1 Oct. 10, 2013

(51) Int. Cl.
*G01M 15/02* (2006.01)
*F02D 45/00* (2006.01)

(52) U.S. Cl.
USPC .................. 123/445; 73/114.38; 702/25

(58) Field of Classification Search
USPC ............. 123/198 D, 304, 445, 575; 702/25; 73/114.38; 701/29.7, 102, 114
See application file for complete search history.

(56) References Cited

U.S. PATENT DOCUMENTS

| | | | |
|---|---|---|---|
| 4,836,016 A * | 6/1989 | Nakano et al. | 73/114.32 |
| 4,989,570 A * | 2/1991 | Kuribara et al. | 123/494 |
| 5,255,661 A * | 10/1993 | Nankee et al. | 123/674 |
| 8,072,604 B2 * | 12/2011 | Arakawa et al. | 356/436 |
| 8,225,647 B2 * | 7/2012 | Mukai | 73/114.55 |
| 2009/0303466 A1 | 12/2009 | Arakawa et al. | |
| 2011/0215813 A1 * | 9/2011 | Sasai et al. | 324/537 |
| 2012/0227707 A1 * | 9/2012 | Sasai et al. | 123/464 |
| 2013/0019651 A1 * | 1/2013 | Sasaki et al. | 73/1.02 |
| 2013/0019669 A1 * | 1/2013 | Wakao et al. | 73/114.42 |
| 2013/0268209 A1 * | 10/2013 | Tashima et al. | 702/25 |

FOREIGN PATENT DOCUMENTS

| | | |
|---|---|---|
| JP | 4-203434 | 7/1992 |
| JP | 3011605 | 3/1995 |
| JP | 2000-303898 | 10/2000 |
| JP | 2008-14741 | 1/2008 |
| JP | 2009-191650 | 8/2009 |
| JP | 2010-38052 | 2/2010 |

* cited by examiner

*Primary Examiner* — Mahmoud Gimie
*Assistant Examiner* — David Hamaoui
(74) *Attorney, Agent, or Firm* — Finnegan, Henderson, Farabow, Garrett & Dunner, LLP

(57) ABSTRACT

An abnormality detection device for an internal combustion engine is controlled according to properties of employed fuel, and capable of accurately detecting an abnormality in a fuel property sensor, and more particularly, a stuck fuel property sensor. A measurement section of the sensor is housed in a fuel container, which is not disposed in a main flow path of a fuel flow path connecting a fuel pump to an injector, but is disposed apart from the main flow path. Fuel drawn from a fuel tank is introduced into the fuel container. The resulting output value of the sensor is acquired as a first sensor output value. Further, the fuel is discharged from the fuel container. The resulting output value of the sensor is acquired as a second output value. The first and second sensor output values are then used to check for an abnormality in the sensor.

14 Claims, 7 Drawing Sheets

ABNORMALITY DETECTION DEVICE FOR INTERNAL COMBUSTION ENGINE

CROSS-REFERENCE TO RELATED APPLICATIONS

This application is a national phase application of International Application No. PCT/JP2010/073760, filed Dec. 28, 2010, the content of which is incorporated herein by reference.

TECHNICAL FIELD

The present invention relates to an abnormality detection device for an internal combustion engine whose operation is controlled in accordance with the properties of employed fuel, and more particularly to an abnormality detection device capable of detecting an abnormality of a fuel property sensor used for fuel property determination.

BACKGROUND ART

An internal combustion engine capable of using fuels having different properties is mounted in a so-called FFV (flexible-fuel vehicle). Ethanol-blended gasoline may be typically used with such an FFV internal combustion engine. When the ethanol-blended gasoline is used as a fuel for an internal combustion engine, it is necessary to adjust an air-fuel ratio in accordance with the concentration of ethanol in the fuel because the ethanol greatly differs from gasoline in calorific value per unit volume. Therefore, an internal combustion engine using the ethanol-blended gasoline has an ethanol concentration sensor, which is a fuel property sensor for determining the properties of an employed fuel, or more specifically, the ethanol concentration in the employed fuel. It is preferred that a capacitance sensor, an optical transmission sensor, or an optical refractive-index sensor be used as the ethanol concentration sensor.

The ethanol concentration measured by the ethanol concentration sensor is used as a parameter for internal combustion engine air-fuel ratio control. This makes it possible not only to obtain a desired torque but also to ensure satisfactory emission performance without regard to the ethanol concentration in the employed fuel.

As described above, the fuel property sensor in the FFV internal combustion engine plays an important role to ensure the expected performance of the internal combustion engine. However, there is no guarantee that the fuel property sensor will function normally at all times, as is the case with the other sensors. Wiring disconnection, short-circuiting, sensor element deterioration, or other abnormality may occur in the fuel property sensor. If, in such an instance, the internal combustion engine is controlled by using an output value of the fuel property sensor, the internal combustion engine fails to operate appropriately in accordance with the properties of the employed fuel, thereby degrading the performance characteristics of the internal combustion engine such as emission performance and fuel efficiency.

It is therefore demanded that an abnormality in the fuel property sensor be accurately detected to immediately repair or replace the fuel property sensor or take other appropriate remedial action. In view of the above circumstances, a technology disclosed in JP-A-2010-038052 (hereinafter referred to as Patent Document 1) presets an upper-limit threshold value and a lower-limit threshold value for the output value of an ethanol concentration sensor. When the output value is outside the range between the upper- and lower-limit threshold values, this technology concludes that the ethanol concentration sensor is abnormal. As the output value of the ethanol concentration sensor varies with fuel temperature even when the ethanol concentration remains unchanged, this technology can change the upper- and lower-limit threshold values in accordance with the fuel temperature measured by a fuel temperature sensor.

However, the technology disclosed in Patent Document 1 does not accurately detect an abnormality in the ethanol concentration sensor at all times. A phenomenon called "stuck" is an abnormality that is likely to occur particularly in the ethanol concentration sensor and will greatly affect the control of the internal combustion engine. In this phenomenon, the output value of the ethanol concentration sensor is stuck at a fixed value. However, this phenomenon may also occur when the output value of the ethanol concentration sensor is between the upper- and lower-limit threshold values. Therefore, the technology disclosed in Patent Document 1 may fail to detect this phenomenon as an abnormality.

A method of detecting a stuck of a capacitance temperature is well-known, as described in JP-A-2000-303898 (hereinafter referred to as Patent Document 2). The method described in Patent Document 2 calculates the difference between a maximum water temperature and a minimum water temperature, which are measured by the temperature sensor after startup of an internal combustion engine. When the calculated difference is small, this method concludes that the sensor is stuck. However, it is difficult to apply this method to the detection of a stuck ethanol concentration sensor. The reason is that, unlike fuel temperature, the ethanol concentration in fuel cannot be changed without refueling.

When the output characteristics of the ethanol concentration sensor relative to the fuel temperature, which are described in Patent Document 1, are taken into account, whether or not the ethanol concentration sensor is stuck can be determined by checking whether the output value of the ethanol concentration sensor varies with the fuel temperature. However, if the ethanol concentration in the employed fuel is 0%, the output value of the ethanol concentration sensor remains substantially unchanged even when the fuel temperature varies. Therefore, the above-described method cannot determine whether the ethanol concentration in the employed fuel is 0% or the sensor is stuck.

Another method of detecting an abnormality in the fuel property sensor is described in JP-A-2008-014741 (hereinafter referred to as Patent Document 3). The abnormality detection method described in Patent Document 3 presumes that the inlet of a fuel tank is provided with a measurement chamber, which includes a fuel property sensor. It is also presumed that the level of a signal output from the fuel property sensor varies depending on whether fuel exists in a measurement space within the measurement chamber. When the employed configuration is as described above, no fuel stays in the measurement space under normal conditions. However, when the fuel is supplied to the fuel tank, the fuel temporarily stays in the measurement space. Thus, the fuel in the measurement space changes the signal level output from the fuel property sensor. Therefore, if the fuel property sensor does not output an appropriate signal during refueling, it can be concluded that the fuel property sensor is abnormal.

However, the technology described in Patent Document 3 cannot determine the properties of an employed fuel with adequate accuracy. The information about fuel properties necessary for internal combustion engine control is the information about the properties of the fuel supplied from the fuel tank to the internal combustion engine, or more specifically, the information about the properties of the fuel injected from an injector. The description set forth in Patent Document 3, however, states that fuel properties determined by the fuel property sensor are the properties of the fuel supplied to the fuel tank and not the properties of the fuel injected from the injector. In the FFV internal combustion engine, which can use fuels having different properties, the properties of the fuel in the fuel tank do not always agree with those of a newly supplied fuel. Therefore, it is highly probable that the fuel properties determined by the fuel property sensor based on the technology described in Patent Document 3 may differ from the fuel properties of the fuel injected from the injector. This makes it difficult to provide appropriate air-fuel ratio control in accordance with the properties of an employed fuel.

Further, the technology described in Patent Document 3 cannot detect an abnormality in the fuel property sensor with adequate accuracy, or more specifically, cannot determine with adequate accuracy whether the fuel property sensor is stuck. If, for instance, the output value of the fuel property sensor is stuck at an output level at which no fuel exists in the measurement space, detecting the output level of the fuel property sensor during refueling makes it possible to determine whether the fuel property sensor is stuck. However, if the output value of the fuel property sensor is stuck at an output level at which the fuel exists in the measurement space, the output level remains unchanged during refueling. Therefore, the fuel property sensor is found to be operating normally. In other words, the technology described in Patent Document 3 cannot detect a stuck sensor in such a situation.

As described above, the previously proposed technologies for fuel property sensor abnormality detection do not detect an abnormality in a fuel property sensor with adequate accuracy, or more particularly, do not detect a stuck fuel property sensor with adequate accuracy.

PRIOR ART LITERATURE

Patent Documents

Patent Document 1: JP-A-2010-038052
Patent Document 2: JP-A-2000-303898
Patent Document 3: JP-A-2008-014741
Patent Document 4: Japanese Utility Model Registration No. 3011605

SUMMARY OF THE INVENTION

An object of the present invention is to accurately detect an abnormality in a fuel property sensor in an internal combustion engine whose operation is controlled in accordance with the properties of an employed fuel, and more particularly, to accurately detect whether the fuel property sensor is stuck. To achieve such an object, the present invention provides an abnormality detection device for an internal combustion engine that is described below.

According to the abnormality detection device provided by the present invention, a sensor having distinctive output characteristics, such as a capacitance sensor, an optical transmission sensor, or an optical refractive-index sensor, is used as a fuel property sensor for determining the alcohol concentration, heaviness, and other properties of an employed fuel. The output characteristics of the fuel property sensor are characterized so that the level of an output value varies depending on whether a liquid or a gas exists in a measurement section, and that when a fuel exists in the measurement section, the output value is determined in accordance with the properties of the fuel. According to the abnormality detection device, the fuel property sensor having the above-described output characteristics is not disposed in a primary fuel flow path connecting a fuel pump to an injector, but disposed in such a manner that at least its measurement section is housed in a fuel container positioned apart from the primary fuel flow path. The fuel container can be disposed outside a fuel tank. From the viewpoint of sealing for fuel leakage prevention, however, it is preferred that the fuel container be disposed inside the fuel tank.

When the fuel drawn from the fuel tank is introduced into the fuel container, the abnormality detection device acquires the output value of the fuel property sensor as a first sensor output value. Further, when the introduced fuel is discharged from the fuel container, the abnormality detection device acquires the output value of the fuel property sensor as a second sensor output value. According to the aforementioned output characteristics of the fuel property sensor, the output levels of the above two sensor output values differ from each other when the fuel property sensor is normal. The abnormality detection device judges, in accordance with the above two sensor output values, whether the fuel property sensor is normal.

A concrete method of judging about an abnormality in the fuel property sensor is to compare the difference between the first and second sensor output values against a predetermined reference difference, and judge, in accordance with the result of the comparison, whether the fuel property sensor is normal. When the difference between the first and second sensor output values is smaller than the reference difference, this method concludes that the fuel property sensor is abnormal.

An alternative method is to compare the first sensor output value against a predetermined first threshold value, compare the second sensor output value against a predetermined second threshold value, and judge, in accordance with the results of the comparisons, whether the fuel property sensor is normal. When the first sensor output value is within an abnormal region indicated by the first threshold value or the second sensor output value is within an abnormal region indicated by the second threshold value, this alternative method concludes that the fuel property sensor is abnormal.

Another alternative method is to compare the difference between the first and second sensor output values against a predetermined reference difference, compare the first or second sensor output value against a predetermined threshold value, and judges, in accordance with the results of the comparisons, whether the fuel property sensor is normal. When the difference between the first and second sensor output values is smaller than the reference difference or either the first or second sensor output value is within an abnormal region indicated by the associated threshold value, this alternative method concludes that the fuel property sensor is abnormal.

For a judgment about an abnormality, the abnormality detection device uses two sensor output values having different output levels. Therefore, even when a sensor output value is stuck at a fixed value, the abnormality detection device can accurately detect such a stuck situation as an abnormality. Further, the abnormality detection device is configured so that the fuel subjected to fuel property judgment by the fuel property sensor is the fuel drawn from the fuel tank, as is the case with the fuel supplied to the injector. Therefore, when the fuel property sensor is normal, the operation of the internal combustion engine can be properly controlled in accordance with the properties of the employed fuel.

A scheme for introducing the fuel into the fuel container and a scheme for discharging the fuel from the fuel container can be as described below.

First of all, the fuel can be forcibly discharged from the fuel container, for example, by applying a negative pressure. However, the fuel in the fuel container is naturally discharged from a fuel outlet simply when the fuel outlet is provided at the bottom of the fuel container with an air inlet provided at the top of the fuel container. In this situation, the measurement section of the fuel property sensor can be immersed in fuel by loading the fuel container with a larger amount of fuel than the amount of fuel discharged from the fuel outlet. In this instance, air may remain in the measurement section. However, when the measurement section is provided with an air outlet for expelling the air upward, the air can be expelled from an area surrounding the measurement section to fully immerse the measurement section in the fuel. Meanwhile, the measurement section of the fuel property sensor can be exposed to air by loading the fuel container with a smaller amount of fuel than the amount of fuel discharged from the fuel outlet or by shutting off the fuel supply to the fuel container. When the fuel discharge from the fuel container is to be actively controlled, a fuel outlet valve may be connected to the fuel outlet to control the opening and closing of the fuel outlet valve.

As regards the introduction of the fuel into the fuel container, it is preferred that the fuel container be disposed at an outlet of a fuel flow path in which a pressure-regulating valve is installed. The pressure-regulating valve is installed in a subsidiary flow path, which branches off from the primary flow path. The pressure-regulating valve opens and closes to automatically adjust the pressure of the fuel flowing in the primary flow path. While the fuel pump is operating after internal combustion engine startup, the pressure-regulating valve remains open to introduce the fuel into the fuel container. After the fuel pump is stopped upon internal combustion engine shutdown, the pressure-regulating valve closes to shut off the fuel supply to the fuel container. When the above-described scheme is employed as the means for introducing the fuel into the fuel container, it is possible to use a fuel property sensor output value acquired at the time of ignition switch turn-off as the first sensor output value and use a fuel property sensor output value acquired at the time of ignition switch turn-on subsequent to internal combustion engine shutdown as the second sensor output value. An alternative is to use a fuel property sensor output value acquired at the time of ignition switch turn-on as the second sensor output value and use a fuel property sensor output value acquired after a predetermined time elapse subsequent to ignition switch turn-on as the first sensor output value.

When, on the other hand, the fuel introduction into the fuel container is to be actively controlled, a subsidiary flow path, which branches off from the primary flow path, may be connected to the fuel container and provided with a fuel inlet valve to control the opening and closing of the fuel inlet valve. In this instance, opening the fuel inlet valve introduces the fuel pumped by the fuel pump into the fuel container, and closing the fuel inlet valve shuts off the fuel supply to the fuel container.

An alternative is to install a dedicated fuel delivery pump in addition to the fuel pump and allow the fuel delivery pump to draw the fuel from the fuel tank and supply the fuel to the fuel container. In this instance, operating the fuel delivery pump delivers the fuel from the fuel tank to the fuel container and stopping the fuel delivery pump shuts off the fuel supply to the fuel container. As the fuel delivery pump is dedicated to a specific purpose, it may be operated only when the fuel properties are to be determined.

When the fuel container is disposed inside the fuel tank, the fuel in the fuel tank may enter the fuel container depending on the amount of fuel stored in the fuel tank. If such a situation arises, the second sensor output value, that is, the output value of the fuel property sensor that is generated while the measurement section is exposed to air, cannot be properly obtained. Therefore, it is preferred that the function of fuel property sensor abnormality judgment be disabled depending on the amount of fuel remaining in the tank. Whether or not the function is to be disabled can easily be determined by allowing a remaining fuel amount sensor to measure the amount of fuel remaining in the fuel tank and comparing the remaining fuel amount against a predetermined reference remaining amount.

BEST MODE FOR CARRYING OUT THE INVENTION

First Embodiment

A first embodiment of the present invention will now be described with reference to the accompanying drawings.

Figure 1:
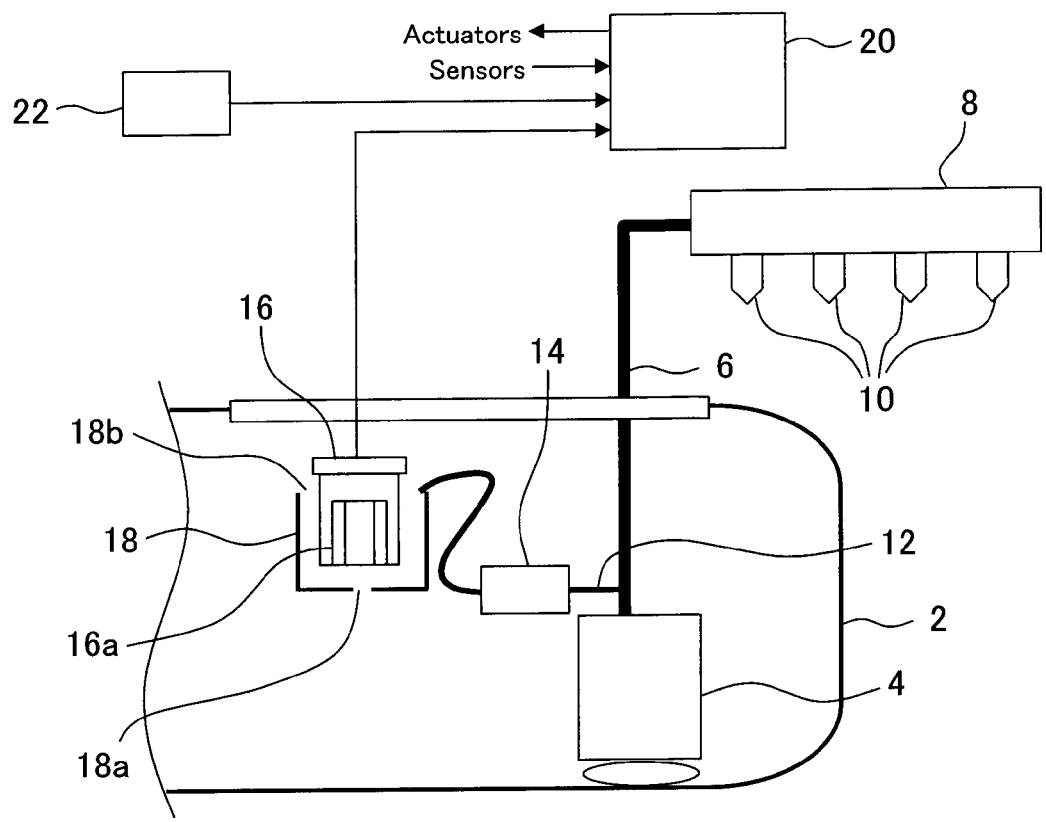
FIG. 1 is a schematic diagram illustrating the configuration of a fuel supply system for an internal combustion engine to which an abnormality detection device according to a first embodiment of the present invention is applied.

An abnormality detection device according to the first embodiment is applied to an FFV internal combustion engine which can use not only gasoline but also ethanol-blended gasoline. FIG. 1 is a schematic diagram illustrating the configuration of a fuel supply system for such an internal combustion engine.

The fuel supply system shown in FIG. 1 is configured so that a main flow path 6 connects a delivery pipe 8 with a fuel pump 4 disposed in a fuel tank 2. The fuel pump 4 is an electrically-operated pump. The main flow path 6 is connected to one end of the delivery pipe 8. A plurality of injectors 10, which are provided for respective cylinders, are connected side by side to the delivery pipe 8. Pressurized fuel pumped from the fuel pump 4 is supplied to the delivery pipe 8 through the main flow path 6, and injected into each cylinder by the injectors 10. In the present embodiment, a fuel flow path which includes the main flow path 6 and the delivery pipe 8 corresponds to the "primary flow path of a fuel flow path" according to the present invention.

In the fuel tank 2, a return flow path 12 branches off from the middle of the main flow path 6. A pressure regulator 14 is disposed in the middle of the return flow path 12. The pressure regulator 14 automatically opens when a fuel pressure in the main flow path 6 exceeds a predetermined relief pressure, and automatically closes when the fuel pressure is not higher than the relief pressure. This ensures that the pressure of the fuel supplied to the injectors 10 is adjusted to a predetermined pressure defined by the relief pressure. While the pressure regulator 14 is open, part of the pressurized fuel pumped from the fuel pump 4 is returned to the fuel tank 2 through the return flow path 12.

Further, a fuel container 18 is disposed in the fuel tank 2 and positioned apart from the main flow path 6. As the fuel container 18 is disposed in an upper part of the fuel tank 2, it is likely to become exposed from a fuel liquid surface. The top of the fuel container 18 is open and used as an air inlet 18b for introducing air into the fuel container 18. There is a hole 18a in the bottom of the fuel container 18. This hole 18a is used as a fuel outlet for discharging the fuel accumulated in the fuel container 18. A leading end of the return flow path 12 is connected to the fuel container 18. The fuel to be returned to the fuel tank 2 through the return flow path 12 is introduced into the fuel container 18 beforehand. The diameter of the fuel outlet 18a is predetermined so that the flow rate of the fuel discharged therefrom does not exceed the flow rate of the fuel introduced from the return flow path 12. If the amount of the introduced fuel exceeds the capacity of the fuel container 18, the fuel overflows from the air inlet 18b disposed at the top of the fuel container 18.

An ethanol concentration sensor 16 is disposed in the fuel container 18. More specifically, the positional relationship between the ethanol concentration sensor 16 and the fuel container 18 is defined so that an electrode section 16a of the ethanol concentration sensor 16 is completely housed within the fuel container 18. The ethanol concentration sensor 16 used in the present embodiment is a capacitance sensor. An output value of the ethanol concentration sensor 16 continuously varies with ethanol concentration. Therefore, the ethanol concentration in an employed fuel can be measured from the output value. The output value of the ethanol concentration sensor 16 is input into an ECU 20 and used as the information for controlling an operation of the internal combustion engine. According to the configuration of the fuel supply system for the present embodiment, the fuel whose ethanol concentration is judged by the ethanol concentration sensor 16 is the fuel drawn from the fuel tank 2 by the fuel pump 4 and the same as the fuel supplied to the injectors 10. Therefore, when the ethanol concentration sensor 16 is normal, an internal combustion engine operation can be properly controlled in accordance with the ethanol concentration in the employed fuel.

The ECU 20 acquires signals from various sensors such as the ethanol concentration sensor 16 and a remaining fuel amount sensor 22. The remaining fuel amount sensor 22 outputs a signal in accordance with the amount of fuel remaining in the fuel tank 2. The remaining fuel amount sensor 22 may employ various sensing methods such as a capacitance sensing method and a float sensing method. In the present embodiment, the sensing method to be employed by the remaining fuel amount sensor 22 is not specifically defined. Upon receipt of signals from various sensors, the ECU 20 controls internal combustion engine operations by operating various actuators in accordance with a predetermined program.

The ECU 20 also functions as the abnormality detection device for the internal combustion engine. When the ECU 20 functions as the abnormality detection device, it detects an abnormality in the ethanol concentration sensor 16 as a detection operation. According to an abnormality detection program incorporated in the ECU 20, the ECU 20 uses the output characteristics of the ethanol concentration sensor 16 to make a judgment about an abnormality. The output characteristics used by the ECU 20 are such that the level of an output value generated from the sensor varies depending on whether a liquid or a gas exists in the electrode section 16a which is a measurement section. These output characteristics are peculiar to capacitance sensors. According to such output characteristics, the sensor output value apparently varies depending on whether the electrode section 16a is immersed in fuel or exposed to air while the ethanol concentration sensor 16 is normal. Therefore, whether the ethanol concentration sensor 16 is normal can be determined by examining the validity of a sensor output value in a case where the electrode section 16a is immersed in fuel and in a case where the electrode section 16a is exposed to air. If the sensor output value is outside an appropriate range in either case, it can be concluded that the ethanol concentration sensor 16 is abnormal.

To use the above-described abnormality judgment method, however, it is necessary to create a state where the electrode section 16a of the ethanol concentration sensor 16 is immersed in fuel and a state where the same section 16a is exposed to air. According to the configuration of the fuel supply system for the present embodiment, such states need not be intentionally created because they are naturally created during a normal vehicle operation.

The state where the electrode section 16a is immersed in fuel is created when the fuel pump 4 operates. When the fuel pump 4 operates to raise the fuel pressure, this makes the pressure regulator 14 open to introduce the fuel into the fuel container 18 from the return flow path 12. When the introduced fuel is accumulated in the fuel container 18, the electrode section 16a is completely immersed in the fuel. The fuel pump 4 operates during an internal combustion engine operation, that is, during the interval between the instant at which an ignition switch is turned on and the instant at which the ignition switch is turned off.

On the other hand, the state where the electrode section 16a is exposed to air is created when the ignition switch is turned off to stop the fuel pump 4. When the fuel pump 4 stops to lower the fuel pressure, the pressure regulator 14 closes to shut off the fuel supply from the return flow path 12 to the fuel container 18. As the fuel supply shuts off while the fuel is continuously discharged from the fuel outlet 18a, the fuel container 18 is emptied of fuel before long so that the electrode section 16a is exposed to air.

As described above, according to the configuration of the fuel supply system for the present embodiment, the information required for abnormality judgment of the ethanol concentration sensor 16 can be obtained by acquiring the output value of the ethanol concentration sensor 16 when the fuel pump 4 is operating and when the fuel pump 4 is stopped. Thus, the ECU 20 which functions as the abnormality detection device performs an abnormality judgment process in accordance with a routine shown in the flowchart of FIG. 2.

Figure 2:
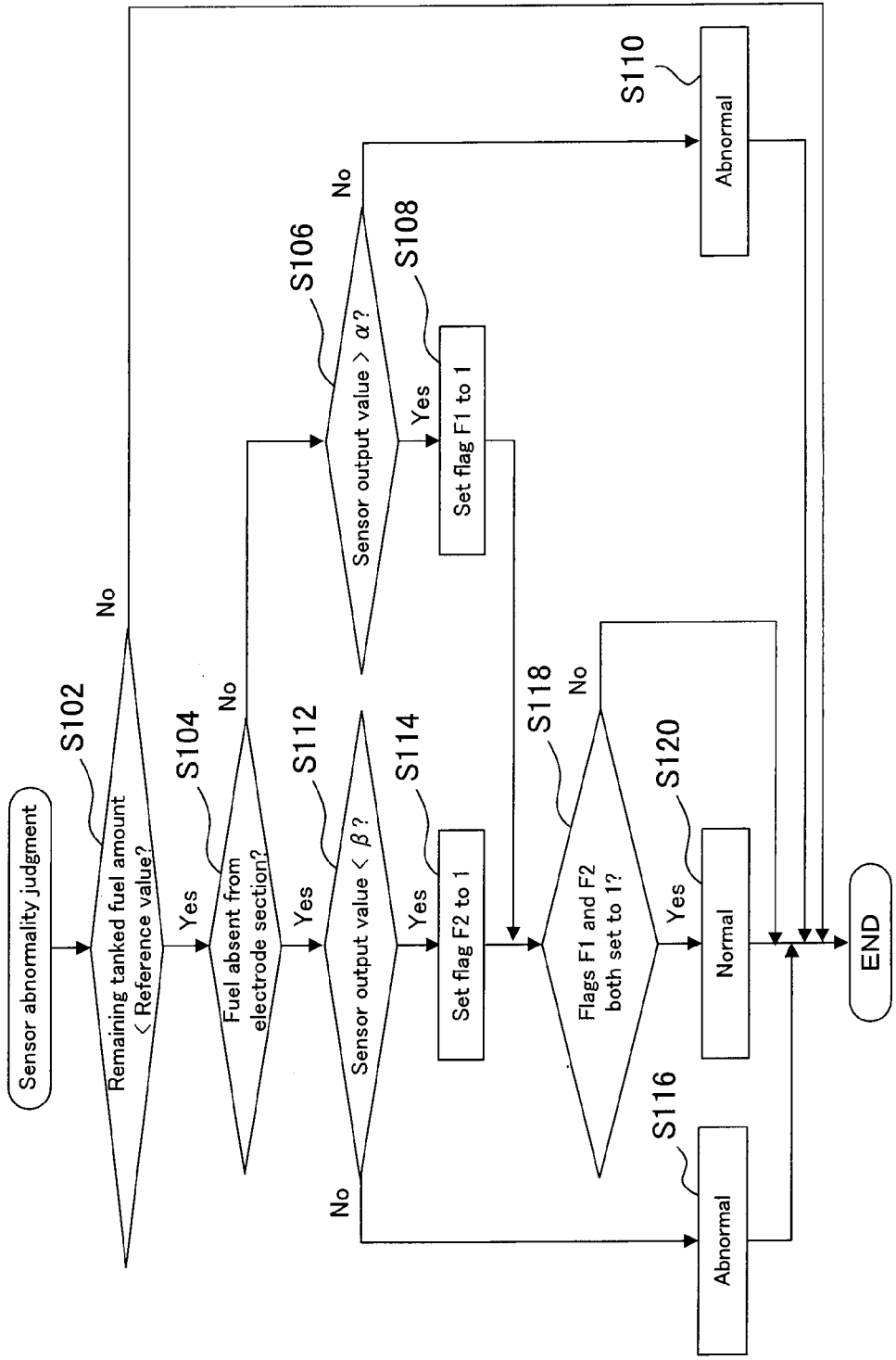
FIG. 2 is a flowchart illustrating an abnormality judgment routine that is executed in the first embodiment of the present invention.

The routine shown in FIG. 2 first performs step S102 in which the amount of remaining fuel is measured by the remaining fuel amount sensor 22 to judge whether the measured remaining fuel amount is smaller than a predetermined reference amount. The reference amount is a remaining fuel amount that serves as a guide for judging whether the fuel tank 2 is loaded with fuel to permit the fuel to enter the fuel container 18. When the remaining fuel amount is larger than the reference amount, the fuel enters the fuel container 18 so that the sensor output value prevailing when the electrode section 16a is exposed to air cannot properly be obtained. Therefore, when the judgment result obtained in step S102 indicates that the remaining fuel amount is larger than the reference amount, the routine inhibits the process of judging whether the ethanol concentration sensor 16 is normal.

When, on the other hand, the judgment result obtained in step S102 indicates that the remaining fuel amount is smaller than the reference amount, the routine proceeds to step S104. In step S104, the routine judges whether the electrode section 16a is emptied of fuel. As mentioned earlier, the fuel supply system for the present embodiment is configured so that the presence of fuel in the electrode section 16a is determined by checking whether the fuel pump 4 is operating or stopped. A state where the electrode section 16a is emptied of fuel is created when the fuel pump 4 stops. A state where the electrode section 16a is loaded with fuel is created when the fuel pump 4 operates.

When the electrode section 16a is loaded with fuel, the routine concludes that the query in step S104 is answered "NO," and then proceeds to step S106. In step S106, the ECU 20 acquires the sensor output value of the ethanol concentration sensor 16. The acquired sensor output value is a sensor output value (a "first sensor output value" according to the present invention) that is obtained when the electrode section 16a is immersed in fuel. The acquired sensor output value is then compared against a predetermined threshold value $\alpha$ (a "first threshold value" according to the present invention). The threshold value $\alpha$ is defined on the basis of a normal sensor output value that is obtained when the electrode section 16a of the ethanol concentration sensor 16 is loaded with fuel. However, the sensor output value obtained when the ethanol concentration sensor 16 is normal varies with the ethanol concentration in the fuel. More specifically, the sensor output value is minimized when the ethanol concentration is 0%. Therefore, the threshold value $\alpha$ is defined on the basis of a sensor output value that is obtained when the ethanol concentration in an employed gasoline is 0%.

When the comparison in step S106 indicates that the sensor output value is greater than the threshold value $\alpha$, the routine sets flag F1 to 1 in step S108. Flag F1 indicates that the ethanol concentration sensor 16 may be normal, and is set to 0 (zero) by default. When, on the other hand, the sensor output value is not greater than the threshold value $\alpha$, there is no doubt that the sensor output value is abnormal. In this instance, the routine concludes in step S110 that the ethanol concentration sensor 16 is abnormal.

When the judgment result obtained in step S104 indicates that the electrode section 16a is emptied of fuel, the routine concludes that the query in step S104 is answered "YES," and then proceeds to step S112. In step S112, the ECU 20 acquires the sensor output value of the ethanol concentration sensor 16. The acquired sensor output value is a sensor output value (a "second sensor output value" according to the present invention) that is obtained when the electrode section 16a is exposed to air. The acquired sensor output value is then compared against a predetermined threshold value $\beta$ (a "second threshold value" according to the present invention). The threshold value $\beta$ is defined on the basis of a normal sensor output value that is obtained when the electrode section 16a of the ethanol concentration sensor 16 is exposed to air.

When the comparison in step S112 indicates that the sensor output value is smaller than the threshold value $\beta$, the routine sets flag F2 to 1 in step S114. Flag F2 indicates that the ethanol concentration sensor 16 may be normal, and is set to 0 (zero) by default. When, on the other hand, the sensor output value is not smaller than the threshold value $\beta$, there is no doubt that the sensor output value is abnormal. In this instance, the routine concludes in step S116 that the ethanol concentration sensor 16 is abnormal.

In step S118, the routine judges whether flags F1 and F2 are both 1. When either of the two flags is 0 (zero) in step S118, the routine does not jump to the conclusion that the ethanol concentration sensor 16 is normal. When flags F1 and F2 are both set to 1, the routine concludes in step S120 that the ethanol concentration sensor 16 is normal.

As described above, the abnormality judgment process performed in the present embodiment uses two sensor output values having different output levels as the information for abnormality judgment and examines the validity of each sensor output value. This makes it possible to accurately judge whether or not the ethanol concentration sensor 16 is normal. Even when the output value of the ethanol concentration sensor 16 is stuck at a fixed value, such a stuck situation can be accurately detected as an abnormality.

From the viewpoint of power consumption and data maintenance, there is a particularly favorable timing when the ECU 20 acquires the output value of the ethanol concentration sensor 16. Such a favorable timing will be described below with reference to FIGS. 3 and 4.

Figure 3:
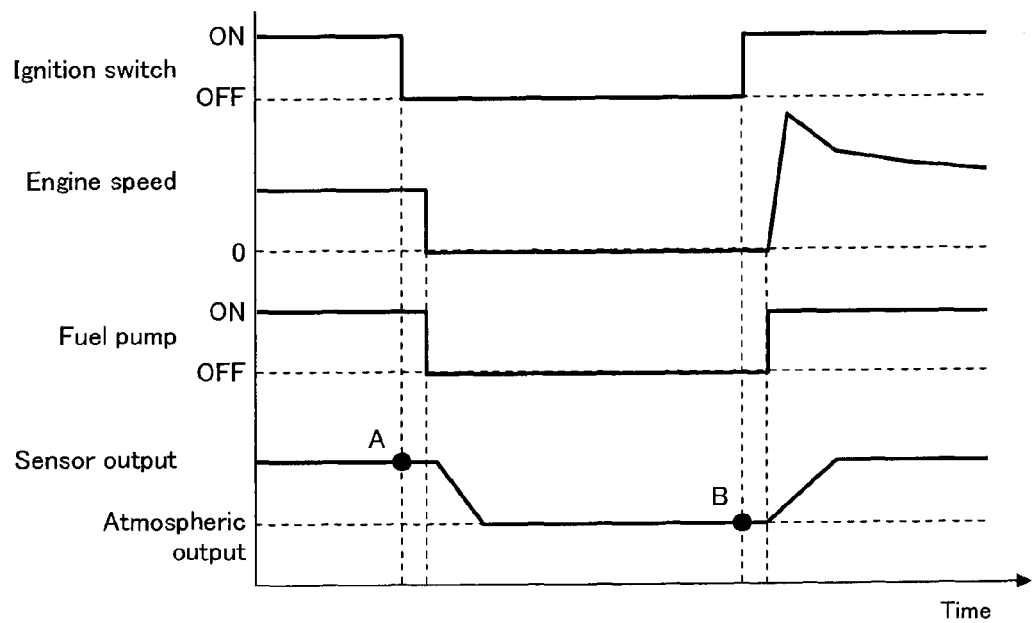
FIG. 3 is a timing diagram illustrating a preferred example of sensor output value acquisition for an abnormality judgment sequence performed in the first embodiment of the present invention.
Figure 4:
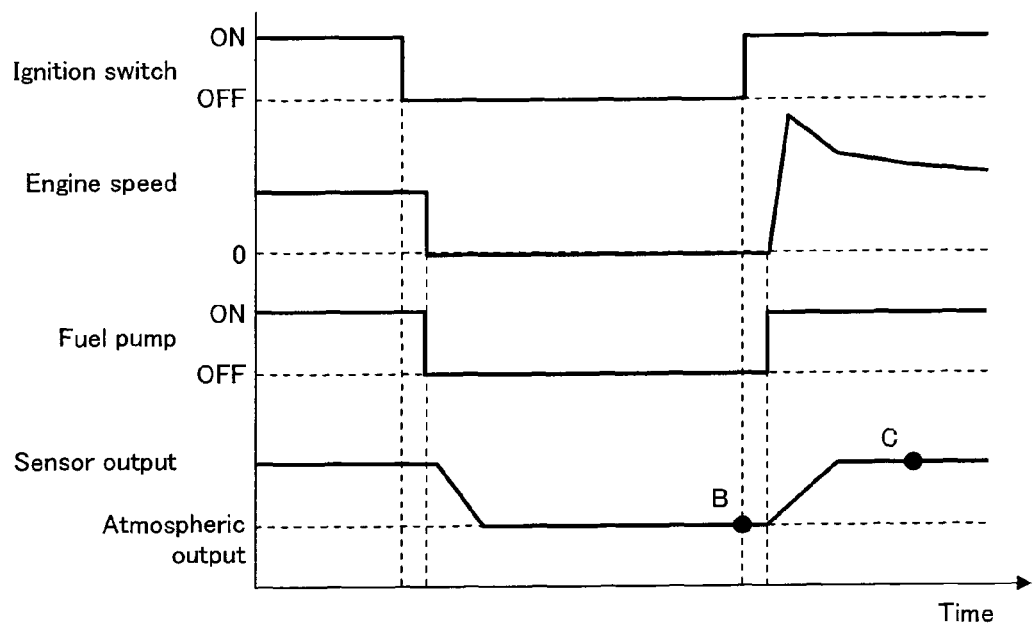
FIG. 4 is a timing diagram illustrating another preferred example of sensor output value acquisition for the abnormality judgment sequence performed in the first embodiment of the present invention.

FIGS. 3 and 4 are timing diagrams that relate to a state where the ethanol concentration sensor 16 is normal and illustrate the relationships between sensor output changes, ignition switch on/off operations, engine speed changes, and fuel pump operation states. As indicated in these figures, a certain amount of elapsed time is required between the instant at which the ignition switch is turned off and the instant at which the output value of the ethanol concentration sensor 16 is equivalent to an atmospheric output (an output value obtained when the electrode section 16a is exposed to air) after the fuel container 18 is emptied of fuel subsequently to stoppage of the fuel pump 4. To let the ECU 20 acquire the sensor output value after ignition switch turn-off, therefore, it is necessary to keep the ECU 20 operating until the fuel container 18 is emptied of fuel. In this instance, the power consumption increases by an amount equivalent to the time required for an extra operation of the ECU 20.

A scheme shown in FIG. 3 is such that the output value of the ethanol concentration sensor 16 is acquired at a timing when the ignition switch is turned off, as indicated by point A. The acquired sensor output value is a sensor output value (the "first sensor output value" according to the present invention) that is obtained when the electrode section 16a is immersed in fuel. Turning off the ignition switch brings the internal combustion engine to a stop. Subsequently, as indicated by point B, the output value of the ethanol concentration sensor 16 is acquired at a timing when the ignition switch is turned back on. The acquired sensor output value is a sensor output value (the "second sensor output value" according to the present invention) that is obtained when the electrode section 16a is exposed to air. This scheme eliminates the necessity of operating the ECU 20 after ignition switch turn-off, thereby avoiding an increase in the power consumption.

On the other hand, a scheme shown in FIG. 4 is such that the output value of the ethanol concentration sensor 16 is acquired at a timing when the ignition switch is turned on, as indicated by point B. The acquired sensor output value is a sensor output value (the "second sensor output value" according to the present invention) that is obtained when the electrode section 16a is exposed to air. Then, as indicated by point C, the output value of the ethanol concentration sensor 16 is acquired again at a timing when a predetermined period of time elapses after ignition switch turn-on. The predetermined period of time is adequate so that a fuel pressure increase caused by an operation of the fuel pump 4 makes the pressure regulator 14 open to let the fuel discharged from the return flow path 12 accumulate in the fuel container 18. The acquired sensor output value is a sensor output value (the "first sensor output value" according to the present invention) that is obtained when the electrode section 16a is immersed in fuel. As is the case with the scheme shown in FIG. 3, this scheme eliminates the necessity of operating the ECU 20 after ignition switch turn-off, thereby avoiding an increase in the power consumption. Further, even when a "battery clear" procedure is performed while the internal combustion engine is stopped, this scheme prevents the loss of data necessary for abnormality judgment.

Second Embodiment

A second embodiment of the present invention will now be described with reference to the accompanying drawings.

As is the case with the abnormality detection device according to the first embodiment, the abnormality detection device according to the second embodiment is applied to an internal combustion engine having the fuel supply system shown in FIG. 1. Therefore, the subsequent description is based on the system shown in FIG. 1, as is the case with the first embodiment.

Figure 5:
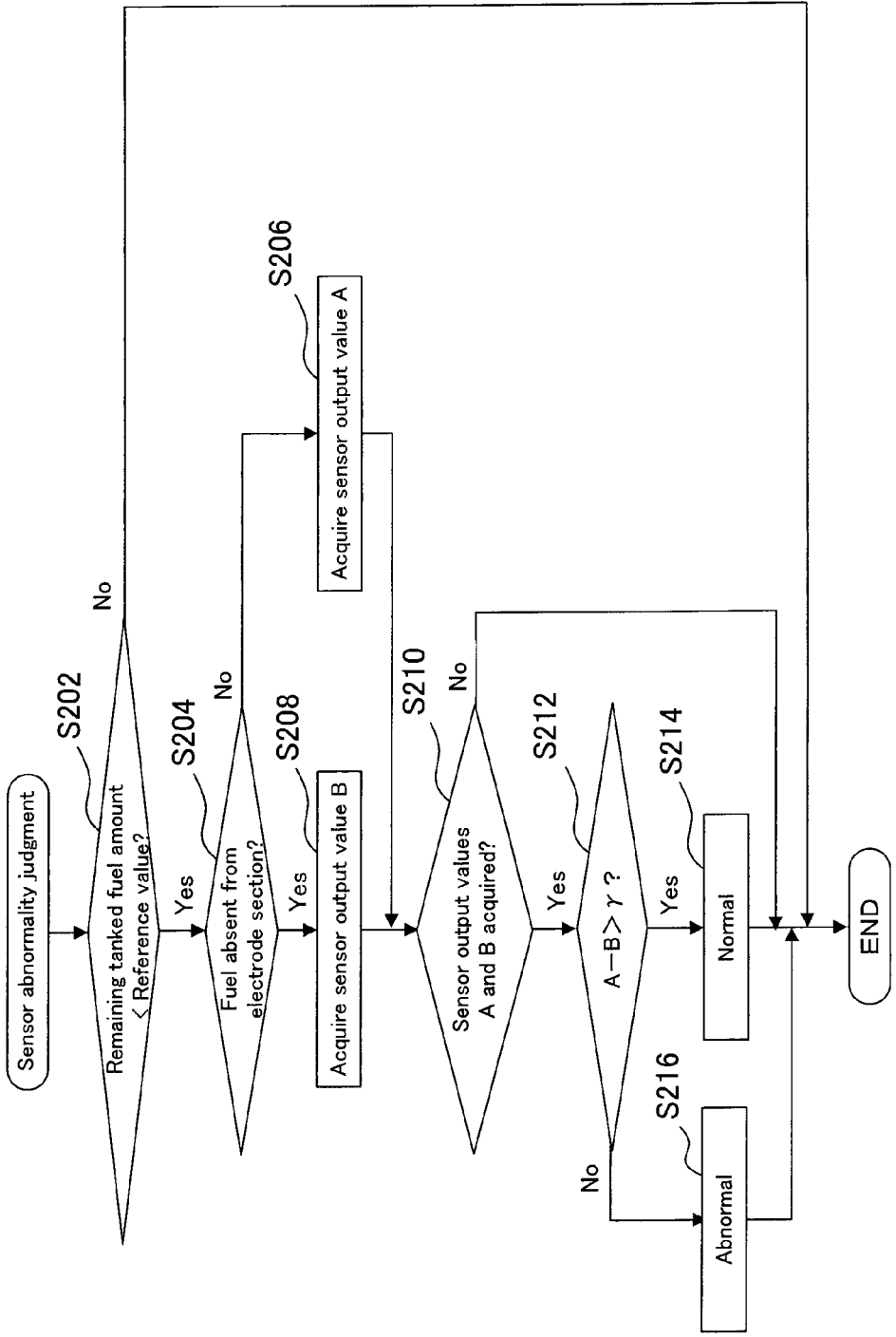
FIG. 5 is a flowchart illustrating an abnormality judgment routine that is executed in a second embodiment of the present invention.

The second embodiment differs from the first embodiment in the abnormality detection function exercised by the ECU 20. More specifically, these two embodiments differ in the method of judgment whether the ethanol concentration sensor 16 is normal. A routine shown in the flowchart of FIG. 5 is executed by the ECU 20 in the second embodiment to perform an abnormality judgment process. This routine will be described below.

The routine shown in FIG. 5 first performs step S202 in which the amount of remaining fuel is measured by the remaining fuel amount sensor 22 to judge whether the measured remaining fuel amount is smaller than a predetermined reference amount. When the judgment result obtained in step S202 indicates that the remaining fuel amount is larger than the reference amount, the routine inhibits the process of judging whether the ethanol concentration sensor 16 is normal.

When, on the other hand, the judgment result obtained in step S202 indicates that the remaining fuel amount is smaller than the reference amount, the routine proceeds to step S204. In step S204, the routine judges whether the electrode section 16a is emptied of fuel. When the electrode section 16a is loaded with fuel, the routine performs step S206. When, on the other hand, the electrode section 16a is emptied with fuel, the routine performs step S208.

In steps S206 and S208, the ECU 20 acquires the sensor output value of the ethanol concentration sensor 16. Sensor output value A which is acquired in step S206 is a sensor output value (the "first sensor output value" according to the present invention) that is obtained when the electrode section 16a is immersed in fuel. Sensor output value B which is acquired in step S208 is a sensor output value (the "second sensor output value" according to the present invention) that is obtained when the electrode section 16a is exposed to air.

Next, the routine proceeds to step S210 and checks whether sensor output values A and B are both acquired. When either of these two sensor output values is still not obtained in step S210, the routine does not proceed to the next step and refrains from making judgment about an abnormality. When, on the other hand, sensor output values A and B are both acquired, the routine proceeds to step S212.

In step S212, the difference between sensor output values A and B is calculated and compared against a predetermined reference difference γ. The reference difference γ is determined on the basis of the difference between sensor output values A and B that should arise when the ethanol concentration sensor 16 is normal. Specifically, when the ethanol concentration sensor 16 is normal, the difference between sensor output values A and B varies with the ethanol concentration in the fuel and is minimized when the ethanol concentration is 0%. Therefore, the reference difference γ is set on the basis of a sensor output value obtained when the ethanol concentration in an employed fuel is 0%.

When the comparison in step S212 indicates that the difference between sensor output values A and B is greater than the reference difference γ, the routine proceeds to step S214 and concludes that the ethanol concentration sensor 16 is normal. When, on the other hand, the difference between sensor output values A and B is not greater than the reference difference γ, the routine proceeds to step S216 and concludes that the ethanol concentration sensor 16 is abnormal, or more specifically, stuck.

As described above, the abnormality judgment process performed in the present embodiment uses two sensor output values (sensor output values A and B) having different output levels as the information for abnormality judgment. Therefore, even when the output value of the ethanol concentration sensor 16 is stuck at a fixed value, such a stuck situation can be accurately detected as an abnormality.

Third Embodiment

A third embodiment of the present invention will now be described with reference to the accompanying drawings.

Figure 6:
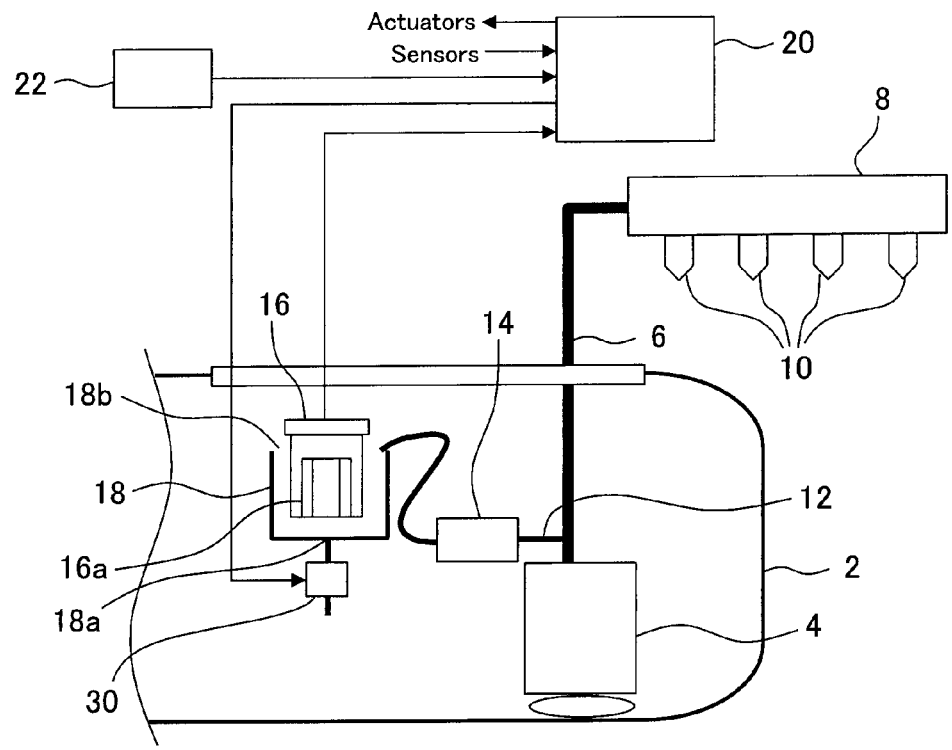
FIG. 6 is a schematic diagram illustrating the configuration of a fuel supply system for an internal combustion engine to which the abnormality detection device according to a third embodiment of the present invention is applied.

The abnormality detection device according to the third embodiment is characterized in that the fuel supply system to which the abnormality detection device is applied has a distinctive configuration. FIG. 6 is a schematic diagram illustrating the configuration of the fuel supply system for an internal combustion engine to which the abnormality detection device according to the present embodiment is applied. In FIG. 6, elements identical with those of the fuel supply system shown in FIG. 1 are designated by the same reference numerals as the corresponding elements.

The present embodiment differs from the first embodiment in that the fuel outlet 18a of the fuel container 18 is provided with a fuel outlet valve 30. The fuel outlet valve 30 is a solenoid valve or a mechanical valve that is operated by fuel pressure. The opening and closing of the fuel outlet valve 30 is controlled by a signal generated from the ECU 20. When the fuel outlet valve 30 closes, the fuel introduced into the fuel container 18 from the return flow path 12 is stored in the fuel container 18. The fuel stored in the fuel container 18 is discharged from the inside of the fuel container 18 to the fuel tank 2 when the fuel outlet valve 30 opens. When the fuel outlet valve 30 is open, the maximum flow rate of fuel dischargeable therefrom is higher than the flow rate of fuel introduced from the return flow path 12. More specifically, while the fuel outlet valve 30 is open, the fuel does not stay in the fuel container 18 no matter whether the fuel flows into the fuel container 18 from the return flow path 12.

The fuel supply system for the present embodiment is configured so that the ECU 20 can intentionally create a state where the fuel container 18 is loaded with fuel and a state where the fuel container 18 is emptied of fuel by controlling the opening and closing of the fuel outlet valve 30. This makes it possible to judge whether or not the ethanol concentration sensor 16 is normal at an arbitrary timing without regard to the operating status of the internal combustion engine. Specifically, the ECU 20 may perform the abnormality judgment process as indicated in either the flowchart of FIG. 2 or the flowchart of FIG. 5.

Fourth Embodiment

A fourth embodiment of the present invention will now be described with reference to the accompanying drawings.

Figure 7:
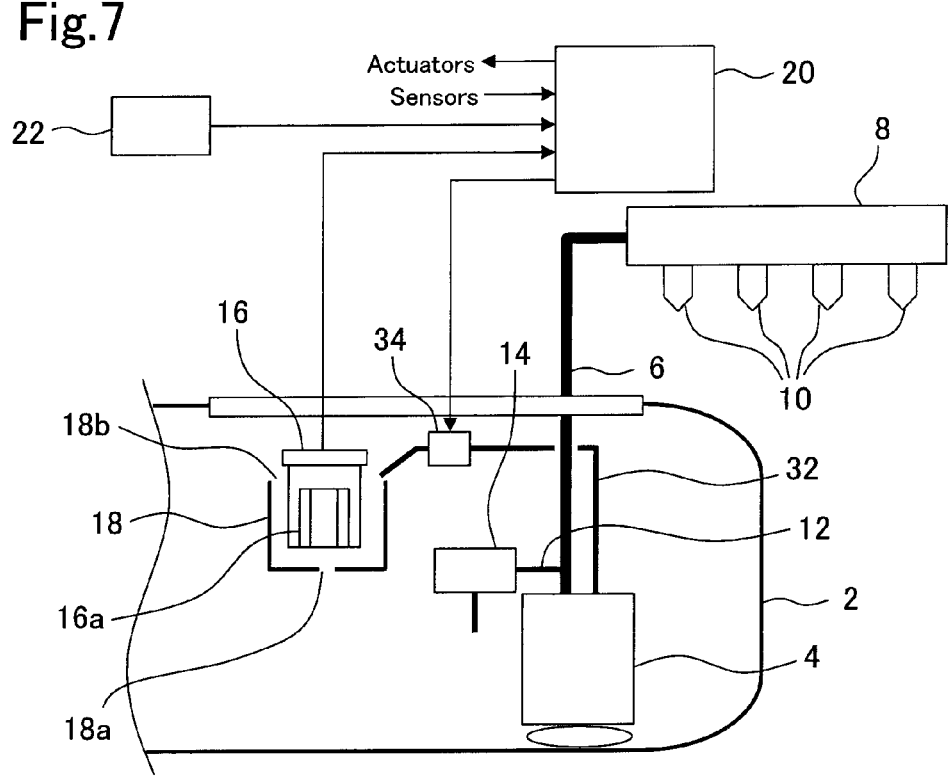
FIG. 7 is a schematic diagram illustrating the configuration of a fuel supply system for an internal combustion engine to which the abnormality detection device according to a fourth embodiment of the present invention is applied.

The abnormality detection device according to the fourth embodiment is characterized in that the fuel supply system to which the abnormality detection device is applied has a distinctive configuration. FIG. 7 is a schematic diagram illustrating the configuration of the fuel supply system for an internal combustion engine to which the abnormality detection device according to the present embodiment is applied. In FIG. 7, elements identical with those of the fuel supply system shown in FIG. 1 are designated by the same reference numerals as the corresponding elements.

The present embodiment differs from the first embodiment in that a dedicated flow path 32 for introducing fuel into the fuel container 18 (hereinafter referred to as the fuel introduction flow path) is provided in addition to the return flow path 12. The fuel introduction flow path 32 is a subsidiary flow path that branches off from the main flow path 6 which is a primary flow path in the fuel pump 4. Therefore, part of the fuel pressurized by the fuel pump 4 is supplied to the fuel introduction flow path 32. A fuel inlet valve 34 whose opening and closing are controlled by a signal from the ECU 20 is installed in the fuel introduction flow path 32. When the fuel inlet valve 34 opens, the fuel pressurized by the fuel pump 4 is introduced into the fuel container 18 from the fuel introduction flow path 32 so that the fuel is stored in the fuel container 18. When, on the other hand, the fuel inlet valve 34 closes, the fuel supply from the fuel introduction flow path 32 to the fuel container 18 shuts off so that the fuel stored in the fuel container 18 is discharged from the fuel outlet 18a to the fuel tank 2.

The fuel supply system for the present embodiment is configured so that the ECU 20 can intentionally create a state where the fuel container 18 is loaded with fuel and a state where the fuel container 18 is emptied of fuel by controlling the opening and closing of the fuel inlet valve 34. This makes it possible to judge whether or not the ethanol concentration sensor 16 is normal at an arbitrary timing without regard to the operating status of the internal combustion engine, as is the case with the third embodiment. Specifically, the ECU 20 may perform the abnormality judgment process as indicated in either the flowchart of FIG. 2 or the flowchart of FIG. 5.

Fifth Embodiment

A fifth embodiment of the present invention will now be described with reference to the accompanying drawings.

Figure 8:
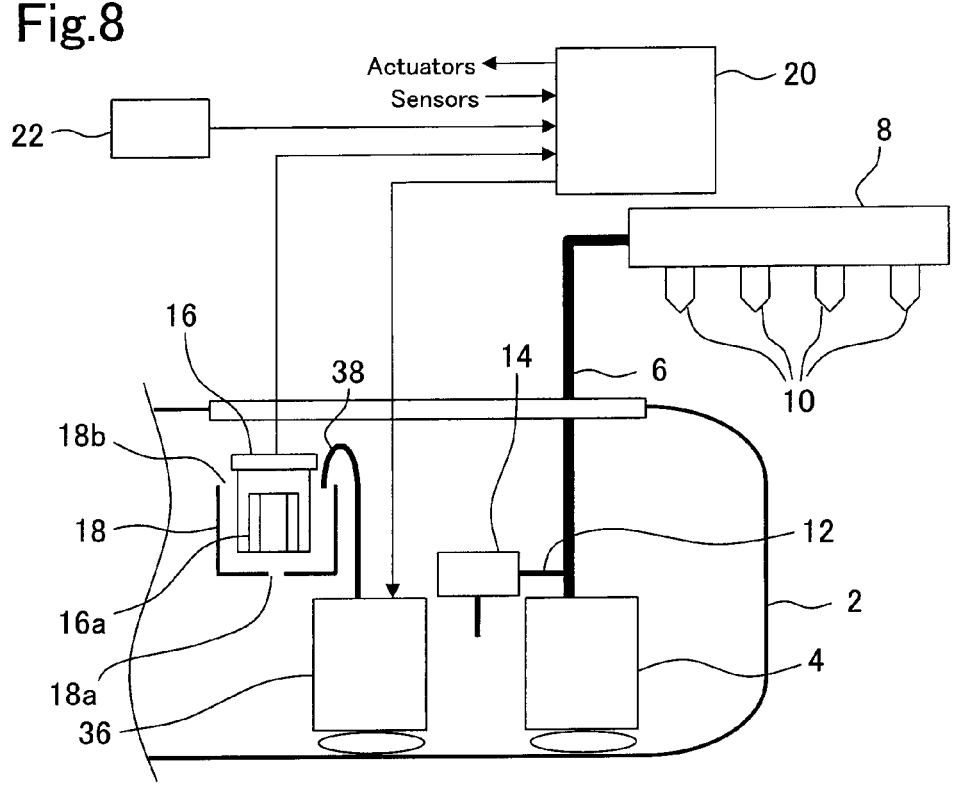
FIG. 8 is a schematic diagram illustrating the configuration of a fuel supply system for an internal combustion engine to which the abnormality detection device according to a fifth embodiment of the present invention is applied.

The abnormality detection device according to the fifth embodiment is characterized in that the fuel supply system to which the abnormality detection device is applied has a distinctive configuration. FIG. 8 is a schematic diagram illustrating the configuration of the fuel supply system for an internal combustion engine to which the abnormality detection device according to the present embodiment is applied. In FIG. 8, elements identical with those of the fuel supply system shown in FIG. 1 are designated by the same reference numerals as the corresponding elements.

The present embodiment differs from the first embodiment in that a dedicated pump 36 (hereinafter referred to as the fuel delivery pump) whose operation is controlled by the ECU 20 is provided. The fuel delivery pump 36 is connected to the fuel container 18 through a dedicated flow path (hereinafter referred to as the fuel introduction flow path) 38. When the fuel delivery pump 36 operates, the fuel pressurized by the fuel delivery pump 36 is introduced into the fuel container 18 from the fuel introduction flow path 38 so that the fuel is stored in the fuel container 18. When, on the other hand, the fuel delivery pump 36 stops, the fuel supply from the fuel introduction flow path 38 to the fuel container 18 shuts off so that the fuel stored in the fuel container 18 is discharged from the fuel outlet 18a to the fuel tank 2.

The fuel supply system for the present embodiment is configured so that the ECU 20 can intentionally create a state where the fuel container 18 is loaded with fuel and a state where the fuel container 18 is emptied of fuel by controlling the operation of the fuel delivery pump 36. This makes it possible to judge whether or not the ethanol concentration sensor 16 is normal at an arbitrary timing without regard to the operating status of the internal combustion engine, as is the case with the third and fourth embodiments. Specifically, the ECU 20 may perform the abnormality judgment process as indicated in either the flowchart of FIG. 2 or the flowchart of FIG. 5.

Other

While the invention has been described in conjunction with preferred embodiments, it should be understood that the present invention is not limited to those preferred embodiments. The preferred embodiments may be variously modified to implement the present invention without departing from the spirit thereof.

For example, the fuel outlet valve 30 used in the third embodiment is also applicable to the fuel supply system for the fourth and fifth embodiments. When the fuel container 18 is provided with the fuel outlet valve 30, their fuel supply system can control the discharge of fuel from the fuel container 18.

Figure 9:
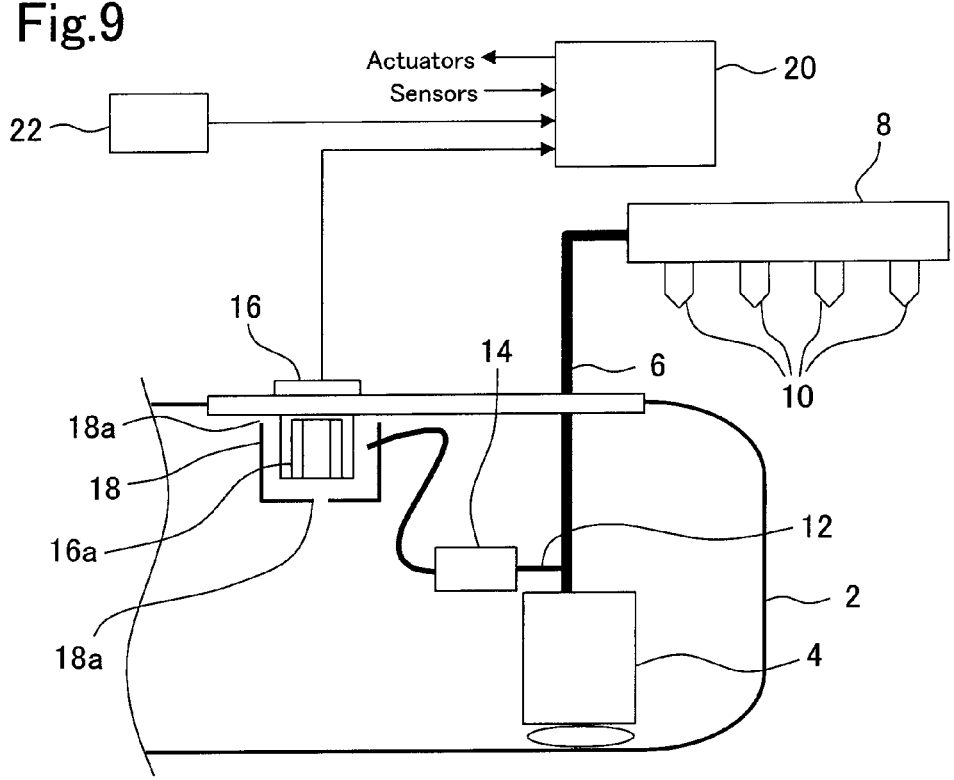
FIG. 9 is a schematic diagram illustrating a modified example of a position at which an ethanol concentration sensor is disposed.

The foregoing embodiments are configured so that the ethanol concentration sensor 16 is disposed in the fuel tank 2 together with the fuel container 18. In contrast to a situation where the ethanol concentration sensor 16 and the fuel container 18 are disposed outside the fuel tank 2, this configuration is at an advantage in that sealing can easily be made to prevent fuel leakage. Alternatively, however, the ethanol concentration sensor 16 may be mounted on the fuel tank 2 with the fuel container 18 disposed in the fuel tank 2, as shown in FIG. 9. In such an instance, the electrode section 16a of the ethanol concentration sensor 16 should be housed in the fuel container 18.

Figure 10:
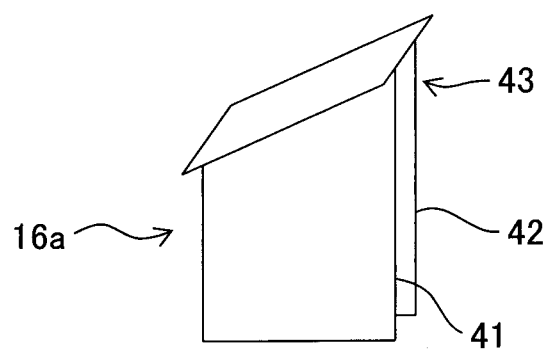
FIG. 10 is a diagram illustrating a preferred example structure of an electrode section of the ethanol concentration sensor.
Figure 11:
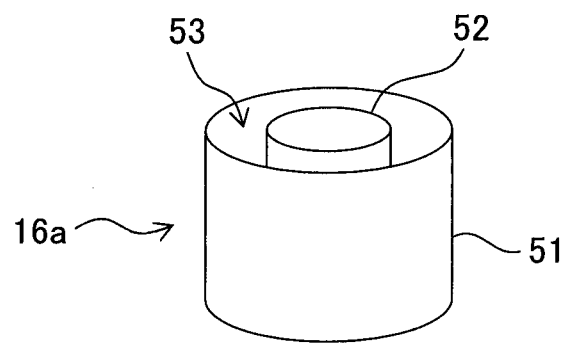
FIG. 11 is a diagram illustrating a preferred example structure of the electrode section of the ethanol concentration sensor.

A particular structure of the electrode section 16a of the ethanol concentration sensor 16 is preferred from the viewpoint of sensor output value accuracy. FIGS. 10 and 11 show preferred exemplary structures of the electrode section 16a. The electrode section 16a shown in FIG. 10 is structured so that an air release section 43 is placed over a space sandwiched between two plate-like electrodes 41 and 42 to expel air upward. The electrode section 16a shown in FIG. 11 is structured so that an air release section 53 is placed over a space enclosed by a cylindrical outer electrode 51 and a cylindrical inner electrode 52 to expel air upward. The use of these structures prevents air from remaining in the electrode section 16a when fuel is introduced into the fuel container 18. This makes it possible to avoid a decrease in sensor output value accuracy.

The two threshold values (threshold values a and M used in the abnormality judgment process according to the first embodiment may be equal to each other. In such an instance, the threshold values should be such that the sensor output value obtained when the electrode section 16a of the ethanol concentration sensor 16 is immersed in fuel is clearly distinguished from the sensor output value obtained when the electrode section 16a is exposed to air.

In the foregoing embodiments, an electrically-operated pump is used as the fuel pump 4. Alternatively, however, the fuel pump 4 may be a mechanical pump driven by the internal combustion engine.

As regards the discharge of fuel from the fuel container 18, the fuel may be forcibly discharged, for instance, by placing the fuel outlet 18a under negative pressure. A jet pump for supplying the fuel in the fuel tank 2 to an inlet of the fuel pump 4 may be used as the means for negative pressure generation.

In the foregoing embodiments, an ethanol concentration sensor is used as the fuel property sensor. However, the type of sensor to be used may be determined in accordance with an employed fuel. If, for instance, the quality of gasoline used in a gasoline engine varies, a sensor for determining whether the employed fuel is heavy or light or a sensor for determining the octane number may be used as the fuel property sensor. Further, when the present invention is to be implemented, the fuel property sensor is not limited to a capacitance sensor. A sensor other than the capacitance sensor, such as an optical refractive-index sensor, may be used as far as it has the output characteristics described earlier.

DESCRIPTION OF REFERENCE NUMERALS

2 Fuel tank
4 Fuel pump
6 Main flow path
8 Delivery pipe
10 Injector
12 Return flow path
14 Pressure regulator
16 Ethanol concentration sensor
16a Electrode section
18 Fuel container
18a Fuel outlet
18b Air inlet
20 ECU
22 Remaining fuel amount sensor
30 Fuel outlet valve
32 Fuel introduction flow path
34 Fuel inlet valve
36 Fuel delivery pump
38 Fuel introduction flow path

The invention claimed is:

1. An abnormality detection device for an internal combustion engine whose operation is controlled in accordance with properties of an employed fuel, the abnormality detection device comprising:
a fuel property sensor whose output value varies in level depending on whether a liquid or a gas exists in a measurement section thereof, the output value being determined in accordance with the properties of the fuel when the fuel exists in the measurement section;
a fuel container that houses the measurement section of the fuel property sensor and is disposed apart from a main flow path of a fuel flow path connecting a fuel pump to an injector;
fuel introduction means for introducing the fuel drawn from a fuel tank into the fuel container;
fuel discharge means for discharging the introduced fuel out of the fuel container;
first sensor output value acquisition means for acquiring a first sensor output value, the first sensor output value being an output value of the fuel property sensor that is generated when the fuel is introduced into the fuel container;
second sensor output value acquisition means for acquiring a second sensor output value, the second sensor output value being an output value of the fuel property sensor that is obtained when the fuel is discharged from the fuel container; and
abnormality judgment means for judging whether or not the fuel property sensor is normal by using the first sensor output value and the second sensor output value as the information for abnormality judgment.

2. The abnormality detection device according to claim 1, wherein the fuel container is disposed in the fuel tank.

3. The abnormality detection device according to claim 2, wherein the fuel discharge means includes:
a fuel outlet disposed at the bottom of the fuel container to discharge the fuel introduced into the fuel container; and
an air inlet disposed at the top of the fuel container to introduce air into the fuel container.

4. The abnormality detection device according to claim 3, wherein the fuel discharge means further includes:
a fuel outlet valve connected to the fuel outlet; and
fuel outlet valve control means for controlling the opening and closing of the fuel outlet valve.

5. The abnormality detection device according to claim 2, wherein the fuel introduction means includes:
a subsidiary flow path that branches off from the main flow path and connects to the fuel container; and
a pressure-regulating valve that opens and closes to automatically adjust the pressure of fuel flowing in the main flow path.

6. The abnormality detection device according to claim 2, wherein the fuel introduction means includes:
a subsidiary flow path that branches off from the main flow path and connects to the fuel container;
a fuel inlet valve disposed in the subsidiary flow path; and
fuel inlet valve control means for controlling the opening and closing of the fuel inlet valve.

7. The abnormality detection device according to claim 2, wherein the fuel introduction means includes:
a fuel delivery pump for drawing fuel from the fuel tank and supplying the fuel to the fuel container; and
fuel delivery pump control means for controlling an operation of the fuel delivery pump.

8. The abnormality detection device according to claim 2, further comprising:
a remaining fuel amount sensor whose output value is determined in accordance with the amount of fuel remaining in the fuel tank;
fuel ingress judgment means for comparing a remaining fuel amount measured from the output value of the remaining fuel amount sensor against a predetermined reference remaining amount to judge whether the fuel tank is loaded with fuel to the extent that the fuel enters the fuel container; and abnormality judgment inhibition means for, when the amount of fuel remaining in the fuel tank is larger than the reference remaining amount, inhibiting the abnormality judgment means from judging whether the fuel property sensor is normal.

9. The abnormality detection device according to claim 5, wherein the first sensor output value acquisition means acquires the output value of the fuel property sensor at a timing when an ignition switch turns off; and
wherein the second sensor output value acquisition means acquires the output value of the fuel property sensor at a timing when the ignition switch turns back on after the internal combustion engine shuts down.

10. The abnormality detection device according to claim 5, wherein the second sensor output value acquisition means acquires the output value of the fuel property sensor at a timing when the ignition switch turns on; and
wherein the first sensor output value acquisition means acquires the output value of the fuel property sensor after a predetermined elapsed time since the ignition switch turned on.

11. The abnormality detection device according to claim 3, wherein the measurement section of the fuel property sensor includes an air release section that expels air upwardly from the measurement section when the fuel container is loaded with fuel.

12. The abnormality detection device according to claim 1, wherein the abnormality judgment means compares the difference between the first sensor output value and the second sensor output value against a predetermined reference difference, and judges, in accordance with the result of the comparison, whether the fuel property sensor is normal.

13. The abnormality detection device according to claim 1, wherein the abnormality judgment means compares the first sensor output value against a predetermined first threshold value, compares the second sensor output value against a predetermined second threshold value, and judges, in accordance with the results of the comparisons, whether the fuel property sensor is normal.

14. An abnormality detection device for an internal combustion engine whose operation is controlled in accordance with properties of an employed fuel, the abnormality detection device comprising:
    a fuel property sensor whose output value varies in level depending on whether a liquid or a gas exists in a measurement section thereof, the output value being determined in accordance with the properties of the fuel when the fuel exists in the measurement section;
    a fuel container that houses the measurement section of the fuel property sensor and is disposed apart from a main flow path of a fuel flow path connecting a fuel pump to an injector;
    a fuel introduction apparatus that introduces the fuel drawn from a fuel tank into the fuel container;
    a fuel discharge apparatus that discharges the introduced fuel out of the fuel container; and
    a controller that is programmed to:
    acquire a first sensor output value, the first sensor output value being an output value of the fuel property sensor that is generated when the fuel is introduced into the fuel container;
    acquire a second sensor output value, the second sensor output value being an output value of the fuel property sensor that is obtained when the fuel is discharged from the fuel container; and
    judge whether or not the fuel property sensor is normal by using the first sensor output value and the second sensor output value as the information for abnormality judgment.

* * * * *